(12) United States Patent
Cheng et al.

(10) Patent No.: US 10,823,720 B2
(45) Date of Patent: Nov. 3, 2020

(54) DEEP SOIL WATER PERCOLATION MONITOR AND MONITORING METHOD THEREFOR

(71) Applicants: Yiben Cheng, Beijing (CN); Wenbin Yang, Beijing (CN)

(72) Inventors: Yiben Cheng, Beijing (CN); Wenbin Yang, Beijing (CN); Lili Wu, Inner Mongolia (CN); Lianxing Yin, Hubei (CN)

(73) Assignees: Wenbin Yang, Beijing (CN); Yiben Cheng, Beijing (CN); Inner Mongolia Low coverage Sand Control Technology Development Co., Ltd., Hohhot (CN)

( * ) Notice: Subject to any disclaimer, the term of this patent is extended or adjusted under 35 U.S.C. 154(b) by 150 days.

(21) Appl. No.: 16/236,233

(22) Filed: Dec. 28, 2018

(65) Prior Publication Data
US 2020/0209210 A1  Jul. 2, 2020

(51) Int. Cl.
*G01N 33/00* (2006.01)
*G01N 33/24* (2006.01)
*A01G 25/16* (2006.01)

(52) U.S. Cl.
CPC ......... *G01N 33/246* (2013.01); *A01G 25/167* (2013.01); *G01N 2033/245* (2013.01)

(58) Field of Classification Search
CPC ........... G01N 33/246; G01N 2033/245; A01G 25/167
See application file for complete search history.

(56) References Cited

U.S. PATENT DOCUMENTS

| | | | |
|---|---|---|---|
| 2005/0121536 A1* | 6/2005 | Bavel | A01G 7/00 239/69 |
| 2015/0223416 A1* | 8/2015 | Eng | G05B 15/02 700/284 |
| 2017/0273259 A1* | 9/2017 | Eng | G05B 15/02 |
| 2018/0170778 A1* | 6/2018 | Liang | C02F 3/327 |

* cited by examiner

*Primary Examiner* — Jamel E Williams
(74) *Attorney, Agent, or Firm* — Wayne & Ken, LLC; Tony Hom (57) ABSTRACT

The present invention discloses a deep soil water percolation monitor and a monitoring method therefor. The monitor includes a soil water balance portion, a flow collection portion, a measurement portion, a water collection portion, a rainfall collecting portion and a control device, wherein the control device includes a central controller, a water inlet pipe, a plugging trough, a drive mechanism, a water level sensor and a humidity sensor. The monitor and monitoring method provided by the present invention can increase the measurement sensitivity of the percolation monitor and increase the measurement accuracy.

10 Claims, 6 Drawing Sheets

DEEP SOIL WATER PERCOLATION MONITOR AND MONITORING METHOD THEREFOR

TECHNICAL FIELD

The present invention relates to the technical field of soil water observation instruments, and in particular to a deep soil water percolation monitor and a monitoring method for extracted layer measurement percolation water samples.

BACKGROUND

At present, there are two main sources for supplementing water on which vegetation in arid and semi-arid zones depends: i.e. meteoric water and ground water. Because sandy soil has relatively good permeability, effective meteoric water often has a significant effect on reallocation of soil water, which not only has significant effect on water of the near-surface sand layer, but has gradually weakened water peaks from the surface to the underground in sequence within a period of time after the rain. Strong rainfall even can directly supply ground water through interception and runoff. For ground water, ground water can be made to rise to effective height through the soil capillarity action, thereby being used by plant root systems. Therefore, it is very important to scientifically and accurately master the water percolation amount in the sandy soil and the percolation process. In arid and semi-arid zones of China, although the rainfall is scarce on the whole, a strong burst of rainfall can form a good infiltration, thereby having a significant effect on supplement of soil water and ground water and forming a fresh water lens.

However there is no good method or instrument for determining the amount of rainfall percolating into the soil layer of a certain depth or supplementing the ground water and the amount of deep percolation water for irrigation, so that the percolation flow passing through the soil layer of a certain depth still cannot be accurately measured.

Therefore, the problem to be urgently solved by those skilled in the art is how to provide a deep soil water percolation monitor which is scientific, efficient and accurate in measurement, and a monitoring method therefor.

SUMMARY

In view of this, the present invention provides a deep soil water percolation monitor and a monitoring method therefor. The present invention can increase the monitoring accuracy of soil percolation amount, simplify the monitoring difficulty, is simple in operation, and is scientific and efficient.

To achieve the above purpose, the present invention adopts the following technical solution:

A deep soil water percolation monitor, comprising: a soil water balance portion, a flow collection portion, a measurement portion, a water collection portion, a rainfall collecting portion and a control device wherein the soil water balance portion is a barrel body provided with an opening at the upper end and a filter screen at the bottom end, and a soil layer consistent with the soil in the region to be measured in particle size and structure is arranged in the barrel body;

the flow collection portion is arranged at the bottom end of the soil water balance portion, the flow collection portion is in a conical structure which is wide at the top and narrow at the bottom, the inner wall of the flow collection portion is coated with a poly tetra fluoroethylene film, and several water percolation holes are provided at the bottom end of the flow collection portion;

the measurement portion is arranged at the bottom of the flow collection portion to measure the percolation water flow collected by the flow collection portion;

the water collection portion is arranged at the bottom end of the measurement portion to drain water and pump water to the surface through the rainfall collecting portion;

the control device includes a central controller, a water inlet pipe, a plugging trough, a drive mechanism, a water level sensor and a humidity sensor, wherein the central controller is connected with the drive mechanism, the water level sensor, the humidity sensor and a water valve of the water inlet pipe respectively, and a water outlet of the water inlet pipe is arranged at the top end of the flow collection portion; the plugging trough is in sealed contact with the water percolation holes of the flow collection portion, the bottom end of the plugging trough is connected with the drive mechanism, the drive mechanism is located between the flow collection portion and the measurement portion, and the drive mechanism is used to drive the plugging trough to open or plug the water percolation holes and drive the plugging trough to be close to or away from the flow collection portion; the water level sensor is located at the top end of the flow collection portion; and the humidity sensor is arranged at the top end of a barrel body of the humidity sensor, and a probe of the humidity sensor is in contact with the topmost end of a soil layer.

By means of the above-mentioned technical solution, the present invention uses the soil water balance portion to increase the sensitivity of percolation water measurement, and uses the control device to automatically adjust the water content saturation of the soil layer in the soil water balance portion, the operation is convenient, and the measurement is accurate.

Preferably, in the deep soil water percolation monitor, the height of the barrel body of the soil water balance portion is consistent with the maximum height of capillary water rise obtained by calculation of particle size and structure of the soil in the region to be measured. For this reason, soil water balance portions with different heights are manufactured for different soil particle sizes, thus having strong targeting and saving materials.

Preferably, in the deep soil water percolation monitor, a flow meter or an electronic balance is arranged in the measurement portion. The percolation amount can be accurately measured, the structure is simple, and the measurement is convenient.

Preferably, in the deep soil water percolation monitor, the water collection portion is provided with a through hole in the position corresponding to the measurement portion, so that it can be guaranteed that the measured water flows into the water collection portion.

Preferably, in the deep soil water percolation monitor, a drain pipe and a peristaltic pump are arranged at the bottom of the water collection portion, and the peristaltic pump is connected with the rainfall collecting portion. The peristaltic pump can pump the soil water sample of the measurement portion, and the drain pipe can drain excessive water, so that the drained water can be effectively processed.

Preferably, in the deep soil water percolation monitor, the water inlet pipe is connected with a water tank and a water pump, and the water pump is used to pump water from the water tank into the water inlet pipe, so that enough water can be provided for wetting soil layer.

Preferably, in the deep soil water percolation monitor, the drive mechanism comprises a first hydraulic rod group and a second hydraulic rod group, wherein the first hydraulic rod group is horizontally arranged, and is connected with the central controller at one end and is vertically connected with the second hydraulic rod group at the other end; and the second hydraulic rod group is connected with the bottom end of the plugging trough. The first hydraulic rod group and the second hydraulic rod group can effectively control the movement of the plugging trough, and are simple in structure and flexible in operation.

The present invention also provides a monitoring method for the deep soil water percolation monitor, specifically comprising the following steps:

S1. Obtaining the maximum height $H_c$ of capillary water rise according to a control equation of the soil water balance portion and the calculation of particle size of soil in the region to be measured, and setting the height of the soil water balance portion as $H_c$;

S2. Filling a soil layer consistent with the soil in the region to be measured in particle size and structure in the barrel body of the soil water balance portion, and adding water to the bottom of the soil layer for wetting, until the water content of the soil layer reaches a saturation state; and S3. When water on the surface percolates into the top of the soil water balance portion, if water percolating into the soil layer breaks the saturation state of the water content of the soil layer and water percolating from the bottom of the soil layer enters the measurement portion (3) through the flow collection portion (2), measuring the percolation amount.

By means of the above-mentioned technical solution, by setting the soil water balance portion of which the water content of the soil layer is in a saturation state, the present invention can increase the measurement sensitivity of the percolation monitor and increase the measurement accuracy.

Preferably, in monitoring method for the deep soil water percolation monitor, the control equation of the soil water balance portion is:

$$Hc = \frac{\sigma n}{\sqrt{2} \, \mu \rho g} \cos\alpha + (1-n)Ha.$$

Through the derivation and calculation of the control equation, the measurement accuracy is increased.

Preferably, in the monitoring method for the deep soil water percolation monitor, the saturation state of water content of the soil layer means that water at the bottom of the soil layer rises to the top of the soil layer through capillary hydraulics and there is no water percolation at both the top and the bottom of the soil layer. This state is an initial state before measurement. In this balance state, if there is soil water percolating into the soil water balance portion before measurement, this balance may be broken, causing saturated soil water at the bottom of the barrel body to be over-saturated and then overflowed. The overflowed water is equal to the amount of percolation water to be measured, and the measurement is more precise.

It can be known form the above-mentioned technical solution that compared with the prior art, the present invention provides a deep soil water percolation monitor and a monitoring method therefor, and has the following advantageous effects:

1. By using the capillary hydraulic principle, the soil water balance portion is added, and the soil layer in the soil water balance portion is water-injected to a saturation state. In this balance state, if there is soil water percolating into the soil water balance portion before measurement, this balance may be broken, causing saturated soil water at the bottom of the barrel body to be over-saturated and then overflowed. The overflowed water is equal to the amount of percolation water to be measured, the sensitivity of measurement of the percolation monitor is increased, and the measurement is more precise.

2. The saturation state of the water content of the soil layer is adjusted by the control device, the water percolation holes at the bottom of the flow collection portion are plugged by the plugging trough to form a sealing structure, and water is injected into the flow collection portion through the water inlet pipe to the bottom end of the soil water balance portion, the bottom end of the soil layer is wetted, until the humidity sensor senses that the top end of the soil layer is wetted, and the soil layer reaches a saturation state. By the adjustment of the control device, it can be guaranteed that the saturation state of the water content of the soil layer is simply and precisely formed, and the operation is convenient.

3. The inner wall of the flow collection portion is coated with a poly tetra fluoroethylene film, to reduce the surface tension of the inner wall, make water fall off more easily, and increase the measurement accuracy.

4. The amount of water percolating from the barrel body of the soil water balance portion is recorded by a flow meter or an electronic balance. When the instrument of the present invention is installed below Xcm depth of the soil to be measured, if the soil layer to be measured produce percolation water because of percolation, the amount of water percolating below Xcm depth from the soil can be measured (or may be called amount of water percolating from X layer), or after rain, according to actual rainfall conditions, it can be judged at what intensity of rainfall percolation water may be produced and how much percolation water can be produced at the intensity, thereby finally determining the amount of water supplementing underground deep layer by rainfall or irrigation in the region to be measured; meanwhile, the present invention can accurately record the percolation flow passing through unit soil layer section within a certain time period and the percolation process, and can accurately analyze migration state of water in the soil layer in combination with the real-time record of the surface rainfall, judge water sources and master water balance, thereby providing a simple and accurate method for deeply analyzing the hydrological characteristics of soil.

BRIEF DESCRIPTION OF DRAWINGS

To more clearly describe the technical solution in the embodiments of the present invention or in the prior art, the drawings required to be used in the description of the embodiments or the prior art will be simply presented below. Apparently, the drawings in the following description are merely the embodiments of the present invention, and for those ordinary skilled in the art, other drawings can also be obtained according to the provided drawings without contributing creative labor.

In the drawings.

1. Soil Water Balance Portion; 2. Flow Collection Portion; 21. Water Percolation Hole; 3. Measurement Portion; 4. Water Collection Portion; 41. Through Hole; 42. Drain Pipe; 5. Rainfall Collecting Portion; 6. Control Device; 61. Central Controller; 62. Water Inlet Pipe; 63. Plugging Trough; 64. Drive Mechanism; 641. First Hydraulic Rod Group; 642. Second Hydraulic Rod Group; 65. Water Level Sensor; 66. Humidity Sensor; 67. Water Valve.

DETAILED DESCRIPTION OF EMBODIMENTS

The technical solution in the embodiments of the present invention will be clearly and fully described below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiment 1

Figure 1:
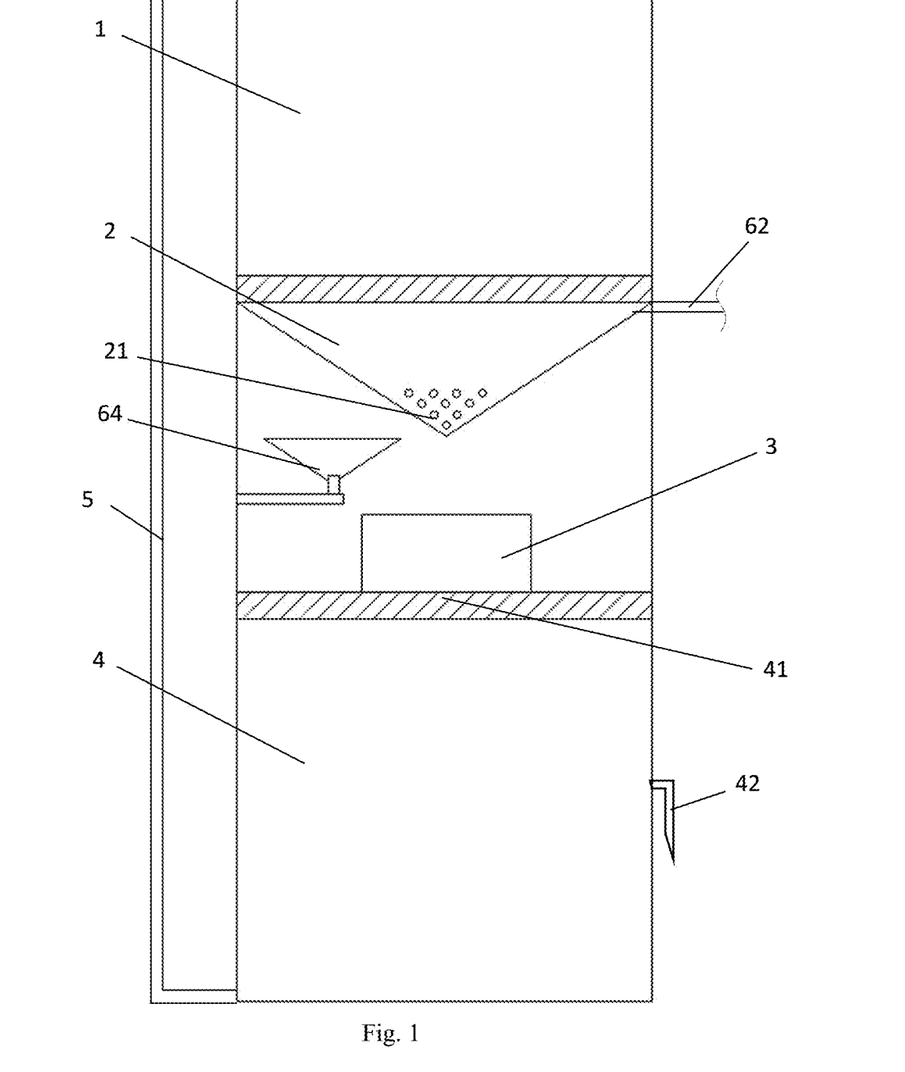
FIG. 1 is a structural schematic diagram showing a measurement state of a percolation monitor provided by the present invention.
Figure 2:
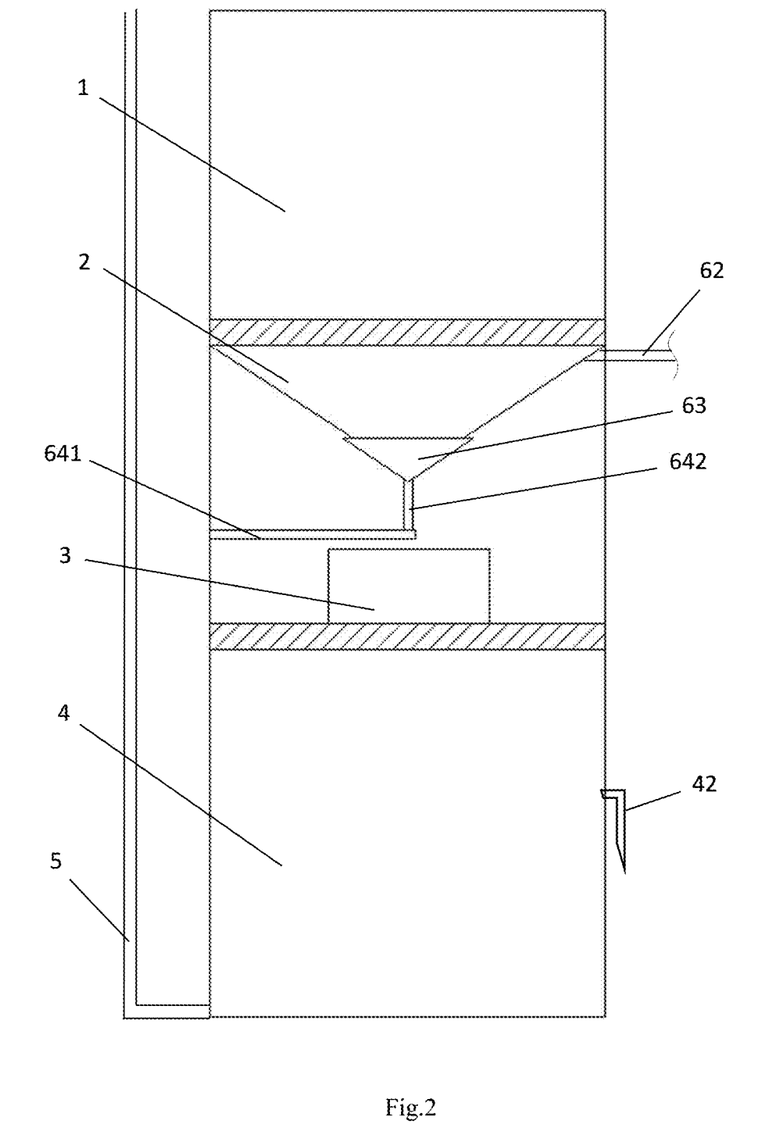
FIG. 2 is a structural schematic diagram showing a state of a soil layer wetted by water injection of a percolation monitor provided by the present invention.
Figure 3:
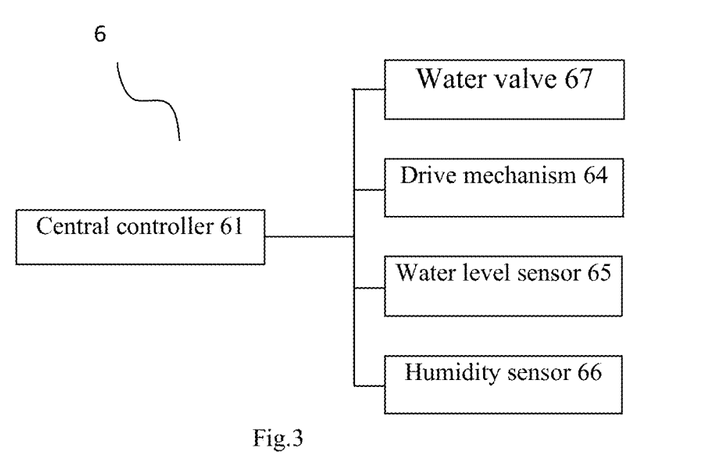
FIG. 3 is a structural schematic diagram showing a control device provided by the present invention.

Referring to FIG. 1 to FIG. 3, this embodiment discloses a deep soil water percolation monitor, including: a soil water balance portion 1, a flow collection portion 2, a measurement portion 3, a water collection portion 4, a rainfall collecting portion 5 and a control device 6.

The soil water balance portion 1 is a barrel body provided with an opening at the upper end and a filter screen at the bottom end, and a soil layer consistent with the soil in the region to be measured in particle size and structure is arranged in the barrel body.

The flow collection portion 2 is arranged at the bottom end of the soil water balance portion 1, the flow collection portion 2 is in a conical structure which is wide at the top and narrow at the bottom, the inner wall of the flow collection portion 2 is coated with a poly tetra fluoroethylene film, and several water percolation holes are provided at the bottom end of the flow collection portion 2.

The measurement portion 3 is arranged at the bottom of the flow collection portion 2 to measure the percolation water flow collected by the flow collection portion 2.

The water collection portion 4 is arranged at the bottom end of the measurement portion 3 to collect percolation water and pump water to the surface through the rainfall collecting portion 5.

The control device 6 includes a central controller 61, a water inlet pipe 62, a plugging trough 63, a drive mechanism 64, a water level sensor 65 and a humidity sensor 66, wherein the central controller 61 is connected with the drive mechanism 64, the water level sensor 65, the humidity sensor 66 and a water valve 67 of the water inlet pipe 62 respectively, and a water outlet of the water inlet pipe 62 is arranged at the top end of the flow collection portion 2; the plugging trough 63 is in sealed contact with the water percolation holes 21 of the flow collection portion 2, the bottom end of the plugging trough 63 is connected with the drive mechanism 64, the drive mechanism 64 is located between the flow collection portion 2 and the measurement portion 3, and the drive mechanism 64 is used to drive the plugging trough 63 to open or plug the water percolation holes 21 and drive the plugging trough 63 to be close to or away from the flow collection portion 2; the water level sensor 65 is located at the top end of the flow collection portion 2; and the humidity sensor 66 is arranged at the top end of a barrel body, and a probe of the humidity sensor 66 is in contact with the topmost end of a soil layer.

To further optimize the above-mentioned technical solution, the height of the barrel body of the soil water balance portion 1 is consistent with the maximum height of capillary water rise obtained by calculation of the particle size and structure of soil in the region to be measured.

To further optimize the above-mentioned technical solution, a flow meter or an electronic balance is arranged in the measurement portion 3.

To further optimize the above-mentioned technical solution, the water collection portion 4 is provided with a through hole 41 in the position corresponding to the measurement portion 3.

To further optimize the above-mentioned technical solution, a drain pipe 42 and a peristaltic pump are arranged at the bottom of the water collection portion 4, and the peristaltic pump is connected with the rainfall collecting portion 5.

The drain pipe 42 is set into an inversed-L shape, to prevent soil from entering the instrument when water is drained and then polluting sample water on long-term basis.

To further optimize the above-mentioned technical solution, the water inlet pipe 62 is connected with a water tank and a water pump, and the water pump is used to pump water from the water tank into the water inlet pipe 62.

To further optimize the above-mentioned technical solution, the drive mechanism 64 comprises a first hydraulic rod group 641 and a second hydraulic rod group 642, wherein the first hydraulic rod group 641 is horizontally arranged, and is connected with the central controller 61 at one end and is vertically connected with the second hydraulic rod group 642 at the other end; and the second hydraulic rod group 642 is connected with the bottom end of the plugging trough 63.

It should be noted that when there is a need to wet the soil layer by water, the central controller 61 drives the first hydraulic rod group 641 and the second hydraulic rod group 642 to make the plugging trough 63 be close to the bottom of the flow collection portion 2, the water percolation holes 21 are plugged and the water valve 67 is opened, water is injected in the flow collection portion 2 through the water inlet pipe 62, when water reaches the top end of the flow collection portion 2, if the water level sensor 65 senses that the water level reaches the highest position, the water valve 67 is closed, water is sucked at the bottom of the soil layer and is transferred to the upper part of the soil layer through the capillary hydraulic action, if the water level sensor 65 senses that the water level of the flow collection portion 2 decreases, the water valve 67 is opened to continue to inject water, until the humidity sensor 66 senses that water reaches the top of the soil layer, the central controller 61 drives the first hydraulic rod group 641 and the second hydraulic rod group 642 to make the plugging trough 63 be away from the bottom of the flow collection portion 2, and measurement is started.

The present invention is compared with the traditional percolation monitor. The traditional percolation monitor adopts a wrapping structure to wrap some or all of the soil to be measured to completely separate same from the surrounding soil, causing that the horizontal soil water exchange process between adjacent soil in the in-situ state is blocked, this defect is magnified when water is injected in the system during manual simulation test, and the actual percolation amount is increased since more soil water can only move in the vertical orientation because of the influence of the side wall. The present invention adopts the important influence factor, i.e. capillary hydraulic lifting height. A soil layer consistent with the soil in the region to be measured in particle size and structure is filled in the body of the soil water balance portion, the length of the barrel body is the capillary hydraulic lifting height, the soil water balance portion has the function that: the soil water at the bottom of soil layer is already saturated, under the condition of standing, soil water may unceasingly percolate until soil water at the bottom of the barrel body reaches the field capacity, and no water percolates any longer at this time. At this moment, because the capillary hydraulic lifting action, the soil water in the barrel body may unceasingly percolate from the opening in the barrel until the soil water at the top of the soil layer cannot percolate from the top under the capillary hydraulic lifting action. The balance state reached at this time is that the soil water content at the bottom of the soil layer is the maximum field capacity, and the capillary hydraulic lifting action makes soil water at the bottom of the soil layer just not percolate from the top of the soil layer. In this balance state, if the soil percolation water caused by rainfall reaches the top of the soil layer and enters the soil water balance portion, the water balance in the soil water balance portion is broken. Because the top of the soil layer is the lower end of the wetting front, soil water can only flow out from the bottom of the lower soil layer until there is no soil water supplement at the top of the soil layer, and the soil water balance portion may reach a new balance state. By means of the method, the amount of water percolating into the target layer can be accurately measured.

Embodiment 2

Referring to FIG. 1 to FIG. 3, this embodiment provides a monitoring method for the deep soil water percolation monitor, specifically comprising the following steps:

S1. Obtaining the maximum height $H_c$ of capillary water rise according to a control equation of the soil water balance portion and the calculation of particle size of soil to be measured, and setting the height of the soil water balance portion as $H_c$;

S2. Filling a soil layer consistent with the soil in the region to be measured in particle size and structure in the barrel body of the soil water balance portion (1), and adding water to the bottom of the soil layer for wetting, until the water content of the soil layer reaches a saturation state; and S3. When water on the surface percolates into the top of the soil water balance portion (1), if water percolating into the soil layer breaks the saturation state of the water content of the soil layer and water percolating from the bottom of the soil layer enters the measurement portion (3) through the flow collection portion (2), measuring the percolation amount.

To further optimize the above technical solution, the control equation of the soil water balance portion is:

$$Hc = \frac{\sigma n}{\sqrt{2}\,\mu\rho g}\cos\alpha + (1-n)Ha.$$

To further optimize the above-mentioned technical solution, the saturation state of water content of the soil layer means that water at the bottom of the soil layer rises to the top of the soil layer through capillary hydraulics and there is no water percolation at both the top and the bottom of the soil layer.

Figure 4:
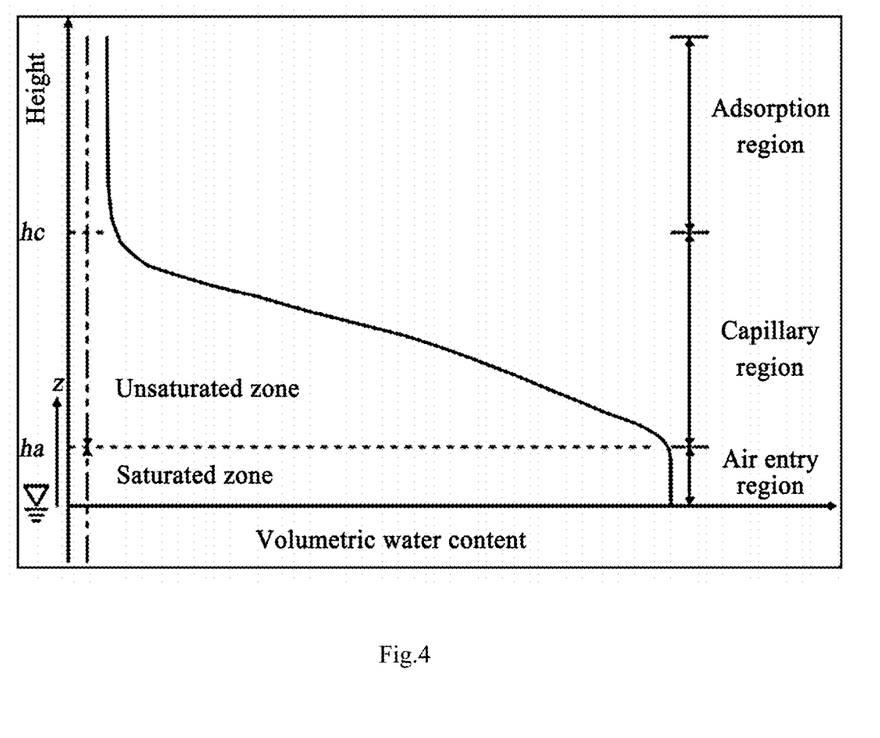
FIG. 4 is a relationship diagram between hydraulic lifting height of capillary water and soil water content provided by the present invention.

The derivation method for the control equation of the soil water balance portion provided by the present invention is as follows:

The driving force of capillary hydraulic lifting can be summarized as the gradient force between the wetting front and the maximum capillary hydraulic lifting height, so that this gradient can be described as:

$$I = \frac{Hc - Z}{Z} \tag{1}$$

where I represents gradient force, $H_c$ represents maximum capillary hydraulic lifting height, and Z represents elevation of wetting front above water head. As shown in FIG. 4, the soil profile can be divided into two portions, i.e. one portion Ha from the surface to the position where air can reach; the other portion where soil water is saturated and below the surface of contact between soil water and air. For the portion below the water level of the saturated soil water, the pressure of pore water is positive, and for the portion above the surface of contact between air and soil water, the pressure of pore water is negative because of the atmospheric pressure. The unsaturated soil portion may be divided into portions as well. According to height $H_c$, one portion is below $H_c$, which is a portion in which the soil water content decreases sharply along with the rise of height; the other portion is above $H_c$, which is higher than $H_c$ so that the soil water content may not vary with the altitude. Within the range of height $H_c$, the water content of unsaturated soil is not uniformly distributed.

Because the hydraulic conductivity coefficients are not linearly distributed, the saturation conductivity of unsaturated soil and the water adsorption of unsaturated soil have always been hot topics in experimental research and theoretical research. When the wetting front above $H_c$ approaches the capillary water, due to the decrease in hydraulic conductivity and the decrease in water adsorption, the change in capillary water holding height is also a tendency to decrease. The non-linear relationship between the hydraulic conductivity coefficients and the soil adsorption can be represented by a mathematical model:

$$K = Ks * f(z) \tag{2}$$

K represents unsaturated hydraulic conductivity coefficient, Ks represents saturated hydraulic conductivity coefficient, Z represents negative value of water head, and f represents mathematical model. Substituting formula 1 into formula 2, the control equation of the hydraulic lifting coefficient of capillary water can be deduced as:

$$\frac{d_s}{d_t} = \frac{k_x f(z)}{n}\frac{h_c - x}{z} \tag{3}$$

where n represents soil porosity, and $H_c$ represents capillary hydraulic lifting height.

Poiseuille law is an equation obtained by Poiseuille in test in 1838. The equation is used to solve the problem of relationship between fluid flow and impact factor, for example, fluid viscosity, pressure gradient of related pipe, pipe length and pipe radius. Assume that water in soil is incompressible and flows at constant speed:

$$Q = \frac{3.14 p\ R^4}{8\ \mu L} \quad (10)$$

where L refers to the length of the pipe space that needs to pass, because pressures in the capillary pipe are different, it can be deduced according to the Poiseuille law:

$$\Delta P = \frac{2\sigma \cos\alpha}{r} - gz\rho_w \quad (11)$$

where σ represents surface tension, α represents contact angle, ρ represents density of water, g represents acceleration of gravity, and r represents capillary radius. Substituting formula 10 into formula 11, the rise speed of capillary water can be deduced as:

$$\frac{dz}{dt} = \frac{r\sigma \cos\alpha}{4p}\frac{1}{z} - \frac{\rho g r^2}{8\mu} \quad (12)$$

according to the hydraulic conductivity coefficient and the Poisseuille law, the hydraulic conductivity coefficient can be adapted into:

$$k = \frac{\rho g r^2}{8\mu} \quad (13)$$

according to the fact that formula 12 and formula 13 represent the same capillary hydraulic lifting speed, the maximum capillary hydraulic lifting height $H_c$ is written as the following formula:

$$Hc = \frac{\sigma n}{4\ \mu k_s}\frac{r\cos\alpha}{f(z)} + \left(1 - \frac{\rho g n}{8\ \mu k_s}\frac{r^2}{f(z)}\right)z \quad (14)$$

Figure 5:
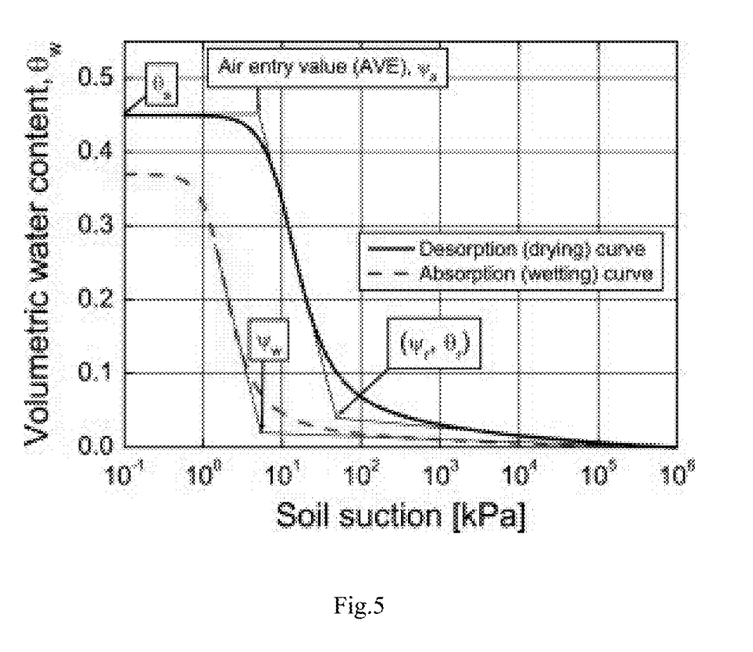
FIG. 5 is a relationship diagram between water content and matric suction in air entry pore provided by the present invention.

To simplify the equation, research personnel draw matric suction of air entry pores (pore air pressure) according to formula (15).

As shown in FIG. 5, according to the research achievements of Chaminda, the water sorption curve of soil is as shown by the dotted part in the Figure, and the water desorption curve is as shown by the black line in the Figure. According to existing research achievements of research personnel, contact angle, air entry height and other parameters can be directly acquired.

Figure 6:
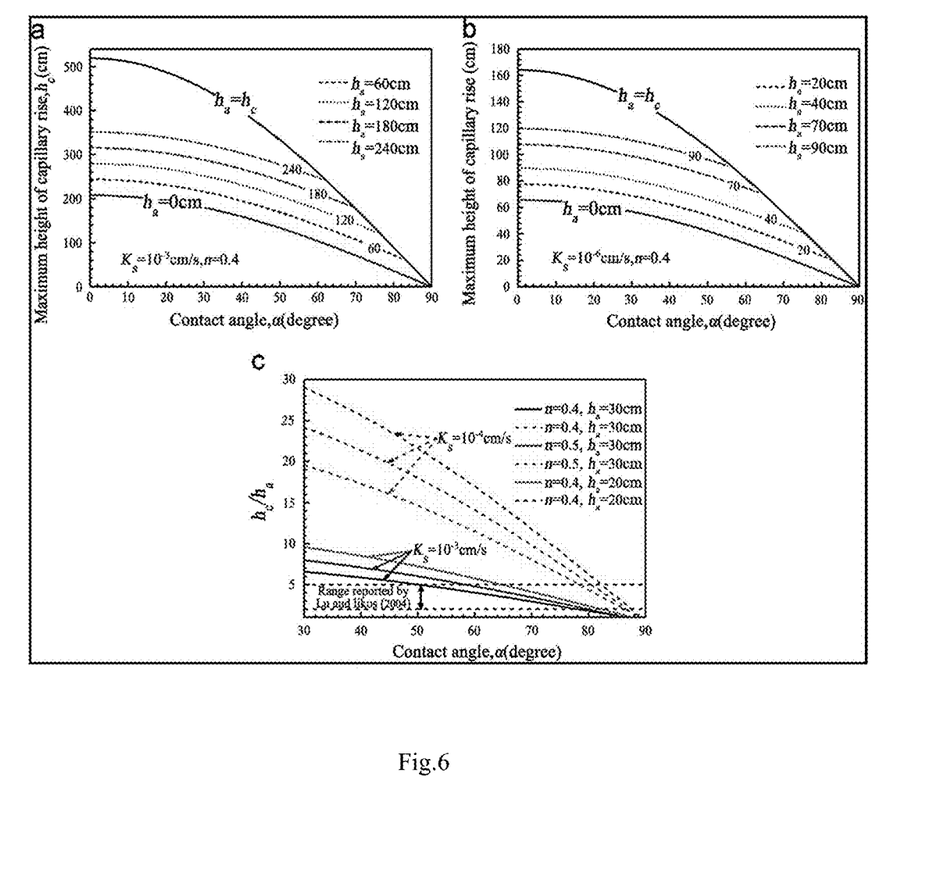
FIG. 6 is a relationship diagram between pore pressure force and contact angle provided by the present invention.

FIG. 6 (*abc*) shows research achievements of parameterization of the maximum hydraulic lifting of capillary height, and FIG. 6 (*ab*) shows the relationship between capillary hydraulic lifting height under different conditions and contact angle. If single pore air pressures Ha are different, curves are parallel. FIG. 6 (*c*) shows the relationship between Hc/Ha and contact angle, simplifying the equation. In the case where pore air pressures are known, the maximum capillary lifting height can be deduced. Similarly, the ratio of Hc/Ha is a variable, which can be represented by a function of soil parameters, for example, saturated hydraulic conductivity and porosity.

Assume that wetting front Z is equal to the air entry height Ha, Formulas (3.10) and (3.11) can be iterated $$Hc = \frac{\sigma n}{\sqrt[2]{2\ \mu \rho g k_z}}\cos\alpha + (1 - n)Ha \quad (15)$$

There is a need to acquire four parameters if the maximum capillary water holding height is acquired according to formula (15), i.e. contact angle (wetting angle), porosity, pore entry height and saturated hydraulic conductivity coefficient. The soil porosity can be directly measured, the saturated hydraulic conductivity can be measured through test, the saturated hydraulic conductivity varies according to the test sample plots, the sampling result can only represent the result of the same region, and the air entry height can be measured through the capillary with an opening. The contact angle is defined as an opening angle at which water droplets meet on the surface of a solid substrate, and contact angle is defined as a constant in general.

To simplify the equation, assume through research that the wetting front Z is equal to the air entry height Ha. Substituting same into formula (15), a simpler formula (16) is obtained, and the result is shown as follows:

$$Hc = \frac{\sigma n}{\sqrt{2\ \mu \rho g}}\cos\alpha + (1 - n)Ha \quad (16)$$

Formula (16) is a calculation equation of the capillary water holding height of the water balance portion (soil structure adjustment portion) of the research calculation instrument. According to the soil samples collected from the four sample plots of the experimental area, according to the fact that the particle size of soil accounting for the largest proportion in each soil sample is a standard particle size, and according to formula (16) of the relationship between the soil particle size and capillary water holding height, the capillary water holding height corresponding to different types of soil may be calculated.

According to soil samples collected from the experimental area and particle size of soil of common types (loam, sandy loam and clay), corresponding capillary water holding height data are calculated. The capillary hydraulic lifting height of the experimental area is 30-77 cm, which is an important parameter for the design of the water balance portion in the deep soil water percolation monitor as a test instrument. The length of the water balance portion of the instrument is equal to the maximum capillary water holding height ($H_c$). During sample plot design, an independent system space can be established if the buried depth of the instrument is designed using the capillary water holding height. The mode of supplementing deep soil water in soil to the upper soil is mainly achieved by the capillary hydraulic lifting action, and after the depth exceeds $H_c$, a partition is formed because the lower soil water cannot supplement the upper soil.

Each embodiment in the description is described in a progressive way. The difference of each embodiment from each other is the focus of explanation. The same and similar parts among all of the embodiments can be referred to each other. For a device disclosed by the embodiments, because the device corresponds to a method disclosed by the embodiments, the device is simply described. Refer to the description of the method part for the related part.

The above description of the disclosed embodiments enables those skilled in the art to realize or use the present invention. Many modifications to these embodiments will be apparent to those skilled in the art. The general principle defined herein can be realized in other embodiments without departing from the spirit or scope of the present invention. Therefore, the present invention will not be limited to these embodiments shown herein, but will conform to the widest scope consistent with the principle and novel features disclosed herein. Therefore, the present invention will not be limited to these embodiments shown herein, but will conform to the widest scope consistent with the principle and novel features disclosed herein.

What is claimed is:

1. A deep soil water percolation monitor, comprising:
a soil water balance portion,
a flow collection portion,
a measurement portion,
a water collection portion,
a rainfall collecting portion, and
a control device,
wherein the soil water balance portion is a barrel body provided with an opening at the upper end and a filter screen at the bottom end; and a soil layer consistent with the soil in the region to be measured in particle size and structure is arranged in the barrel body;
the flow collection portion is arranged at the bottom end of the soil water balance portion; the flow collection portion is in a conical structure which is wide at the top and narrow at the bottom; the inner wall of the flow collection portion is coated with a poly tetra fluoroethylene film; and several water percolation holes are provided at the bottom end of the flow collection portion;
the measurement portion is arranged at the bottom of the flow collection portion to measure percolation water flow collected by the flow collection portion;
the water collection portion is arranged at the bottom end of the measurement portion to collect percolation water and pump water to the surface through the rainfall collecting portion;
the control device comprises:
a central controller,
a water inlet pipe,
a plugging trough,
a drive mechanism,
a water level sensor, and
a humidity sensor, wherein the central controller is connected with the drive mechanism, the water level sensor, the humidity sensor and a water valve of the water inlet pipe, respectively; a water outlet of the water inlet pipe is arranged at the top end of the flow collection portion (2); the plugging trough (63) is in sealed contact with the water percolation holes (21) of the flow collection portion (2), the bottom end of the plugging trough is connected with the drive mechanism; the drive mechanism is located between the flow collection portion and the measurement portion; the drive mechanism is used to drive the plugging trough to open or plug the water percolation holes and drive the plugging trough to be close to or away from the flow collection portion; the water level sensor is located at the top end of the flow collection portion; and the humidity sensor is arranged at the top end of a barrel body; and a probe of the humidity sensor is in contact with the topmost end of a soil layer.

2. The deep soil water percolation monitor of claim 1, wherein the height of the barrel body of the soil water balance portion (1) is consistent with the maximum height of capillary water rise obtained by calculation of the particle size and structure of soil in the region to be measured.

3. The deep soil water percolation monitor of claim 1, wherein a flow meter or an electronic balance is arranged in the measurement portion.

4. The deep soil water percolation monitor of claim 1, wherein the water collection portion is provided with a through hole in the position corresponding to the measurement portion.

5. The deep soil water percolation monitor of claim 1, wherein a drain pipe and a peristaltic pump are arranged at the bottom of the water collection portion; and the peristaltic pump is connected with the rainfall collecting portion.

6. The deep soil water percolation monitor of claim 1, wherein the water inlet pipe is connected with a water tank and a water pump; and the water pump is used to pump water from the water tank into the water inlet pipe.

7. The deep soil water percolation monitor of claim 1, wherein the drive mechanism comprises a first hydraulic rod group and a second hydraulic rod group; the first hydraulic rod group is horizontally arranged, and is connected with the central controller at one end and is vertically connected with the second hydraulic rod group at the other end; and the second hydraulic rod group is connected with the bottom end of the plugging trough.

8. A monitoring method using the deep soil water percolation monitor of claim 1, specifically comprising the following steps:
S1. obtaining the maximum height $H_c$ of capillary water rise according to a control equation of the soil water balance portion and the calculation of particle size of soil in the region to be measured, and setting the height of the soil water balance portion as $H_c$;
S2. filling a soil layer consistent with the soil in the region to be measured in particle size and structure in the barrel body of the soil water balance portion, and adding water to the bottom of the soil layer for wetting, until the water content of the soil layer reaches a saturation state; and
S3. when water on the surface percolates into the top of the soil water balance portion, if water percolating into the soil layer breaks the saturation state of the water content of the soil layer and water percolating from the bottom of the soil layer enters the measurement portion through the flow collection portion, measuring percolation amount.

9. The deep soil water percolation monitor of claim 8, wherein the control equation of the soil water balance portion is:

$$Hc = \frac{\sigma n}{\sqrt{2}\ \mu \rho g}\cos\alpha + (1-n)Ha.$$

10. The deep soil water percolation monitor of claim 8, wherein the water balance portion reaches the state: the water content of the bottom soil layer reaches a saturation state, the capillary hydraulic lifting height is consistent with the height of the balance portion, and there is no water percolation at both the top and the bottom of the soil layer.

* * * * *